US011229442B2

(12) United States Patent
Lampropoulos et al.

(10) Patent No.: US 11,229,442 B2
(45) Date of Patent: Jan. 25, 2022

(54) ULTRASOUND COMPATIBLE INFLATABLE VASCULAR COMPRESSION AND RELATED SYSTEMS AND METHODS (71) Applicant: Merit Medical Systems, Inc., South Jordan, UT (US)

(72) Inventors: Fred Lampropoulos, Salt Lake City, UT (US); Tyler David Rees, Draper, UT (US); Aaron Hopkinson, Herriman, UT (US); Ahmed A. Hassan, Almere (NL)

(73) Assignee: Merit Medical Systems, Inc., South Jordan, UT (US)

( * ) Notice: Subject to any disclaimer, the term of this patent is extended or adjusted under 35 U.S.C. 154(b) by 294 days.

(21) Appl. No.: 16/294,020

(22) Filed: Mar. 6, 2019

(65) Prior Publication Data
US 2019/0274692 A1    Sep. 12, 2019

Related U.S. Application Data (60) Provisional application No. 62/641,041, filed on Mar. 9, 2018.

(51) Int. Cl.
*A61B 17/135* (2006.01)
*A61B 17/132* (2006.01)
*A61B 17/00* (2006.01)

(52) U.S. Cl.
CPC ........ *A61B 17/135* (2013.01); *A61B 17/1325* (2013.01); *A61B 2017/00106* (2013.01);
(Continued)

(58) Field of Classification Search
CPC . A61B 17/135; A61B 17/1325; A61B 17/132; A61B 17/1322; A61B 17/1355;
(Continued)

(56) References Cited

U.S. PATENT DOCUMENTS

| 1,281,653 A | 10/1918 | Plummer |
| 2,332,107 A | 10/1943 | Nieburgs |

(Continued)

FOREIGN PATENT DOCUMENTS

| CN | 201205292 | 3/2009 |
| CN | 201861701 | 6/2011 |

(Continued)

OTHER PUBLICATIONS

Merit Medical Adds 2 New Products for Assisting Hemostasis, Posted at Merit.com, no posting date, retrieved Aug. 26, 2020 online https://www.merit.com/articles/merit-medical-adds-2-new-products-assisting-hemostasis (2020).

(Continued)

*Primary Examiner* — Tan-Uyen T Ho
*Assistant Examiner* — Bridget E. Rabaglia
(74) *Attorney, Agent, or Firm* — Stoel Rives LLP (57) ABSTRACT

Vascular compression devices with an inflatable chamber are disclosed. The inflatable chamber of the vascular compression devices can be inflated and then deflated with a liquid with ultrasound properties similar to biological tissues. Ultrasound waves may be applied to the vascular compression device and may propagate through the vascular compression device and into the biological tissue of the patient to produce an ultrasound image to determine the patency of the vessel.

14 Claims, 6 Drawing Sheets

(52) U.S. Cl.
CPC .............. *A61B 2017/00442* (2013.01); *A61B 2017/00907* (2013.01); *A61B 2017/00942* (2013.01)

(58) Field of Classification Search
CPC ........... A61B 2017/00442; A61B 2017/00924; A61B 5/022; A61B 5/021; A61B 2017/00106; A61F 5/0056
USPC ................................ 606/201, 203, 204, 202
See application file for complete search history.

(56) References Cited

U.S. PATENT DOCUMENTS

| | | | |
|---|---|---|---|
| 3,050,064 A | 8/1962 | Moore et al. | |
| 4,390,519 A | 6/1983 | Sawyer | |
| 4,479,495 A | 10/1984 | Isaacson | |
| 4,557,262 A | 12/1985 | Snow | |
| 5,139,512 A | 8/1992 | Dreiling et al. | |
| 5,269,803 A | 12/1993 | Geary et al. | |
| 5,304,186 A | 4/1994 | Semler et al. | |
| 5,304,201 A | 4/1994 | Rice | |
| 5,613,491 A | 3/1997 | Kanner et al. | |
| 5,728,120 A | 3/1998 | Shani et al. | |
| 5,779,657 A | 7/1998 | Daneshvar | |
| 5,997,564 A | 12/1999 | Shehata et al. | |
| 6,068,646 A | 5/2000 | Lam | |
| 6,231,507 B1* | 5/2001 | Zikorus | A61B 8/04 600/437 |
| 6,833,001 B1 | 12/2004 | Chao | |
| 7,758,574 B2 | 7/2010 | Hijii et al. | |
| 7,780,612 B2 | 8/2010 | Ross | |
| 8,147,417 B2 | 4/2012 | Gavriely | |
| 8,632,840 B2 | 1/2014 | Avitable | |
| 8,845,680 B2 | 9/2014 | Lampropoulos et al. | |
| 9,332,994 B2 | 5/2016 | Pancholy et al. | |
| D804,663 S | 12/2017 | Jenkins | |
| 10,172,625 B2 | 1/2019 | Wada et al. | |
| 10,463,833 B2 | 11/2019 | Clarke et al. | |
| D893,034 S | 8/2020 | Kase et al. | |
| 2003/0055453 A1 | 3/2003 | Akerfeldt | |
| 2003/0149359 A1* | 8/2003 | Smith | A61B 8/4281 600/437 |
| 2005/0113866 A1 | 5/2005 | Heinz et al. | |
| 2005/0125025 A1 | 6/2005 | Rioux | |
| 2006/0058841 A1 | 3/2006 | Mills et al. | |
| 2007/0239092 A1 | 10/2007 | Ross | |
| 2007/0248810 A1 | 10/2007 | McGee et al. | |
| 2007/0270720 A1 | 11/2007 | Fry | |
| 2009/0209896 A1 | 8/2009 | Selevan | |
| 2009/0281565 A1 | 11/2009 | Mcneese | |
| 2010/0217202 A1 | 8/2010 | Clark | |
| 2010/0280541 A1 | 11/2010 | Lampropoulos | |
| 2012/0221041 A1 | 8/2012 | Hansson et al. | |
| 2012/0238934 A1 | 9/2012 | During | |
| 2012/0296369 A1 | 11/2012 | Atthoff et al. | |
| 2013/0023734 A1* | 1/2013 | Okamura | A61B 17/135 606/202 |
| 2013/0079723 A1 | 3/2013 | Andino et al. | |
| 2013/0165787 A1* | 6/2013 | Ukawa et al. | A61B 8/0825 600/443 |
| 2013/0237866 A1* | 9/2013 | Cohen et al. | A61B 17/135 600/502 |
| 2013/0245675 A1 | 9/2013 | Wada et al. | |
| 2013/0289613 A1 | 10/2013 | Wada et al. | |
| 2014/0012120 A1 | 1/2014 | Cohen et al. | |
| 2014/0012313 A1 | 1/2014 | Finkielsztien et al. | |
| 2014/0125718 A1 | 5/2014 | Morrison et al. | |
| 2014/0142615 A1 | 5/2014 | Corrigan, Jr. | |
| 2014/0236221 A1* | 8/2014 | Zhadkevich | A61B 17/135 606/202 |
| 2015/0018869 A1 | 1/2015 | Benz et al. | |
| 2015/0164436 A1 | 6/2015 | Maron et al. | |
| 2015/0201948 A1 | 7/2015 | Kornowski et al. | |
| 2015/0327871 A1* | 11/2015 | Fortson | A61B 17/135 606/202 |
| 2018/0008281 A1 | 1/2018 | Hazama | |
| 2018/0008282 A1 | 1/2018 | Hazama et al. | |
| 2018/0008283 A1 | 1/2018 | Hazama | |
| 2018/0042615 A1 | 2/2018 | Kimura et al. | |
| 2018/0070956 A1 | 3/2018 | Lampropoulos et al. | |
| 2018/0185032 A1 | 7/2018 | Matsushita et al. | |
| 2018/0250017 A1 | 9/2018 | Matsushita et al. | |
| 2018/0280008 A1 | 10/2018 | Okamura | |
| 2019/0021742 A1 | 1/2019 | Hazama | |
| 2019/0029693 A1 | 1/2019 | Okamura | |
| 2019/0046214 A1 | 2/2019 | Hazama | |
| 2019/0133602 A1 | 5/2019 | Kiemeneij et al. | |
| 2020/0029946 A1 | 1/2020 | Green et al. | |

FOREIGN PATENT DOCUMENTS

| | | |
|---|---|---|
| DE | 4006696 | 11/1990 |
| FR | 2828231 | 2/2003 |
| JP | 2013111444 | 6/2013 |
| JP | 6211285 | 10/2014 |
| JP | 6261368 | 8/2015 |
| JP | 6389510 | 9/2015 |
| JP | 6261420 | 11/2015 |
| JP | 2017000259 | 1/2017 |
| JP | 2017000260 | 1/2017 |
| JP | 2017047036 | 3/2017 |
| JP | 2018011798 | 1/2018 |
| JP | 2018011867 | 1/2018 |
| JP | 2018019927 | 2/2018 |
| JP | 2018033602 | 3/2018 |
| JP | 2018075257 | 5/2018 |
| JP | 2018171081 | 11/2018 |
| JP | 2019047956 | 3/2019 |
| JP | 2019166265 | 10/2019 |
| JP | 2019208953 | 12/2019 |
| JP | 2019216947 | 12/2019 |
| JP | 2019217130 | 12/2019 |
| JP | 2020014588 | 1/2020 |
| WO | 2004041313 | 5/2004 |
| WO | 2017043536 | 3/2017 |
| WO | 2018017365 | 1/2018 |

OTHER PUBLICATIONS

Pua, et al.,"Snuffbox" Distal Radial Access, J Vasc Interv Radiol, No. 29:44 ,2018.
Zhou, et al.,Transient Ulnar Artery Compression Facilitates Transradial Access, Medicine, No. 95:48 ,2016.
European Search Report dated Sep. 7, 2017 for EP 09763115.4.
International Search Report and Written Opinion dated Nov. 28, 2017 for PCT/US2017/041726.
International Search Report and Written Opinion dated Dec. 26, 2017 for PCT/US2017/051715.
International Search Report dated Nov. 18, 2009 for PCT/US2009/042868.
MedPlus, Inc., Tourniquet (Radial Artery Compression Device), http://www.bikudo.com/product_search/details/187473/tourniquet_radial_artey_compression_device.html Nov. 24, 2009.
Notice of Allowance dated Jun. 9, 2014 for U.S. Appl. No. 13/741,046.
Notice of Allowance dated Oct. 16, 2012 for U.S. Appl. No. 12/435,227.
Office Action dated Jan. 10, 2019 for U.S. Appl. No. 15/705,759.
Office Action dated Feb. 14, 2014 for U.S. Appl. No. 13/741,046.
Office Action dated Mar. 2, 2011 for U.S. Appl. No. 12/349,405.
Office Action dated Mar. 5, 2013 for U.S. Appl. No. 13/741,046.
Office Action dated Jun. 6, 2016 for U.S. Appl. No. 14/033,177.
Office Action dated Jun. 28, 2011 for U.S. Appl. No. 12/349,405.
Office Action dated Aug. 17, 2012 for U.S. Appl. No. 12/349,405.
Office Action dated Nov. 3, 2015 for U.S. Appl. No. 14/033,177.
Office Action dated Dec. 8, 2011 for U.S. Appl. No. 12/349,405.
Office Action dated Dec. 27, 2016 for U.S. Appl. No. 14/033,177.
International Search Report and Written Opinion dated Jun. 12, 2019 for PCT/US2019/020980.

(56) References Cited

OTHER PUBLICATIONS

Office Action dated Apr. 12, 2021 for U.S. Appl. No. 16/179,257.
Office Action dated Jul. 23, 2021 for U.S. Appl. No. 16/179,257.
Notice of Allowance dated Nov. 25, 2020 for U.S. Appl. No. 29/653,828.
Office Action dated Oct. 8, 2020 for U.S. Appl. No. 16/179,257.

* cited by examiner

ULTRASOUND COMPATIBLE INFLATABLE VASCULAR COMPRESSION AND RELATED SYSTEMS AND METHODS

RELATED CASES

This application claims priority to U.S. Provisional Application No. 62/641,041, filed on Mar. 9, 2018, and titled "Ultrasound Compatible Inflatable Vascular Compression and Related Systems and Methods," which is hereby incorporated by reference in its entirety.

TECHNICAL FIELD

The present disclosure relates generally to the field of medical devices used to provide hemostasis at a vascular access puncture site. More particularly, some embodiments of the present disclosure relate to a hemostasis device used to provide hemostasis of the vasculature following vascular access as well as systems and methods for determining vascular patency.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Numerous medical procedures involve insertion of one or more elongate medical devices into the vasculature of a patient. Some of these interventional procedures involve delivery of a medical device through, for example, a radial artery of the patient. Achieving patient hemostasis during and/or after an interventional procedure that involves puncturing the radial artery (or other portions of the vasculature) may present certain challenges.

To facilitate patient hemostasis at a vascular access site, pressure may be applied directly to, adjacent to, or slightly upstream of the skin puncture site. Such pressure may prevent or reduce the leakage of blood from the vasculature access site and promote hemostasis. Certain embodiments described herein facilitate the application of pressure to promote hemostasis at a radial access site. However, the present disclosure is not so limited; the application of pressure to promote hemostasis may be applied at arteries and veins, in the wrist, hand, arm, foot, and leg, and at other vasculature access points in a patient's body. Additionally, though specific examples in the disclosure below may refer to compression of a radial artery, the embodiments of the present disclosure may be directed to other arteries or veins in a patient, such as arteries and veins within a patient's arm, wrist, hand, leg, or foot. For example, the embodiments of the present disclosure may be configured to compress portions of the femoral artery.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to one another through an intermediate component. The phrase "attached to" refers to interactions between two or more entities which are in direct contact with each other and/or are separated from each other only by a fastener of any suitable variety (e.g., an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a radial artery compression device or a component thereof is the end that is furthest from the attachment point of the arm of the patient during ordinary use of the device. The proximal end refers to the opposite end or the end nearest the patient during ordinary use. When used as a directional term, the term "radial" refers to the direction pointing from the center of the arm or hand to the thumb-side portion of the arm or hand. The term "ulnar" refers to the opposite direction. The particular volumes recited herein refer to the volumes of fluid that are delivered from a syringe that holds the recited amount of fluid at atmospheric pressure. For example, an inflatable chamber has a capacity of 15 mL if it is capable of receiving 15 mL of fluid from a syringe that holds 15 mL of fluid at atmospheric pressure.

Figure 1:
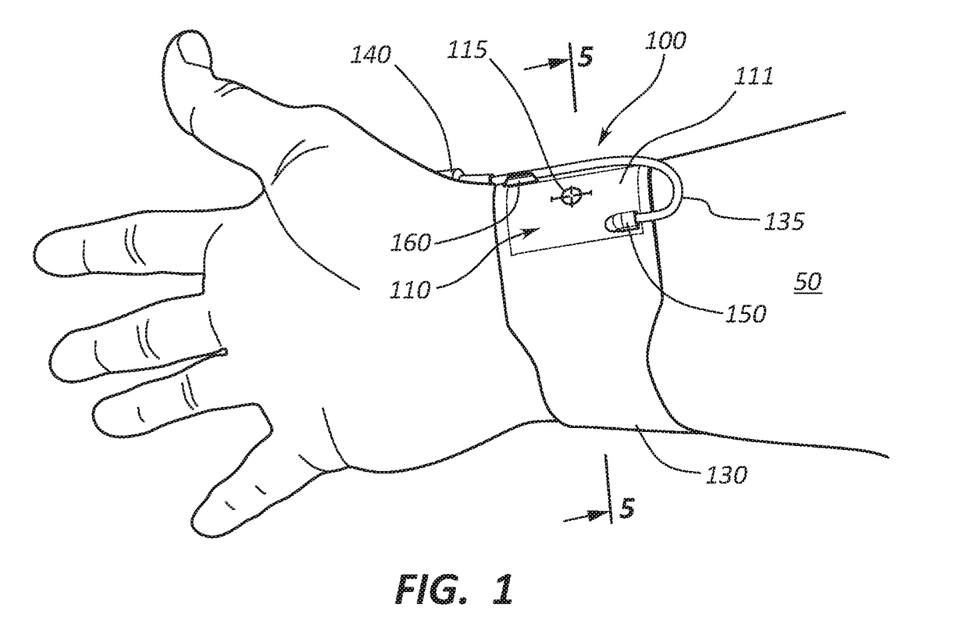
FIG. 1 depicts a vascular compression device coupled to a wrist of a patient.
Figure 2:
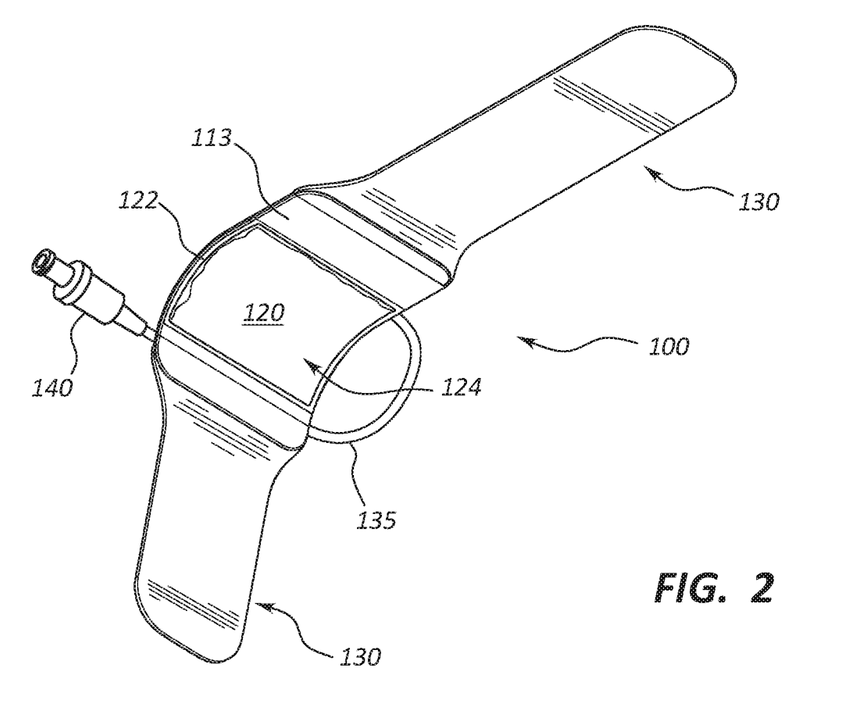
FIG. 2 is a perspective view of an underside of the vascular compression device of FIG. 1.
Figure 3:
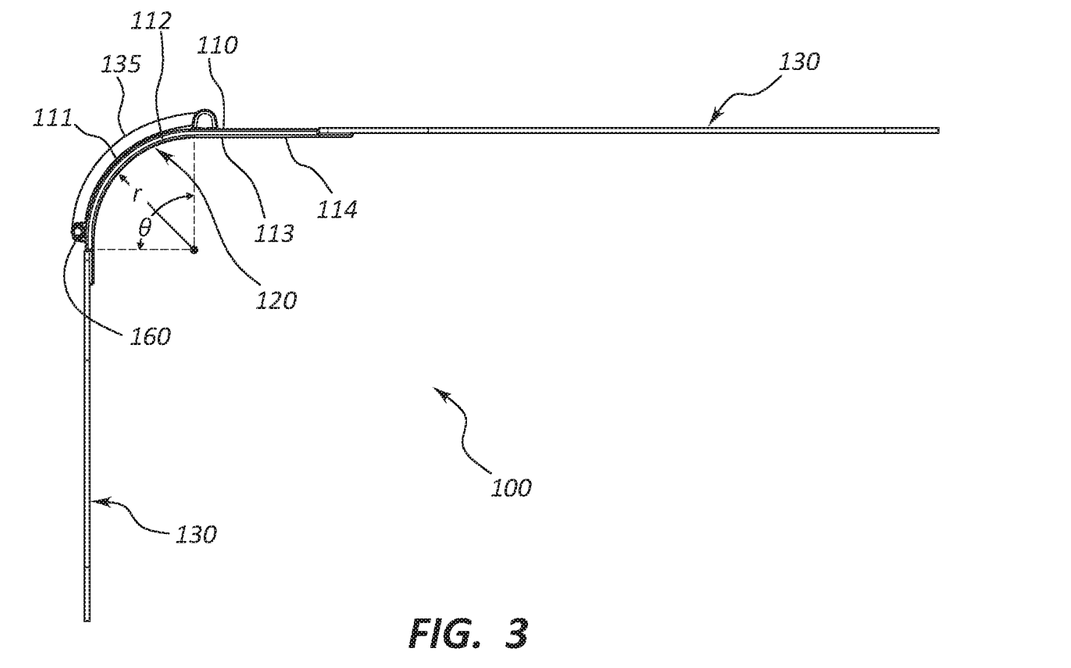
FIG. 3 is a side view of the vascular compression device of FIGS. 1 and 2 with the inflatable chamber in an uninflated state.
Figure 4:
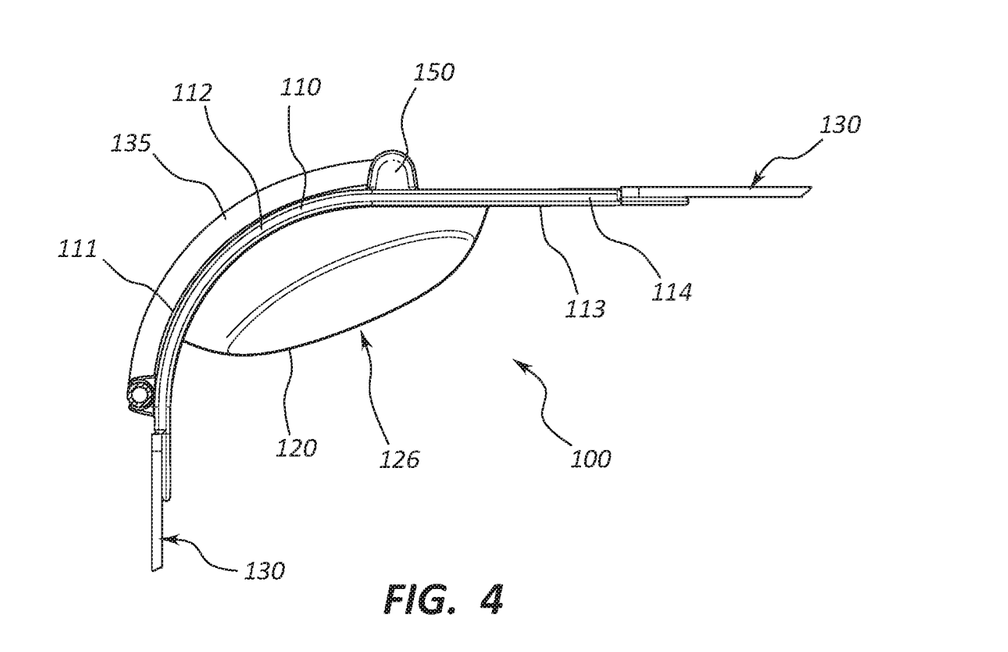
FIG. 4 is a side view of a portion of the vascular compression device of FIGS. 1-3 with the inflatable chamber in an inflated state.
Figure 5:
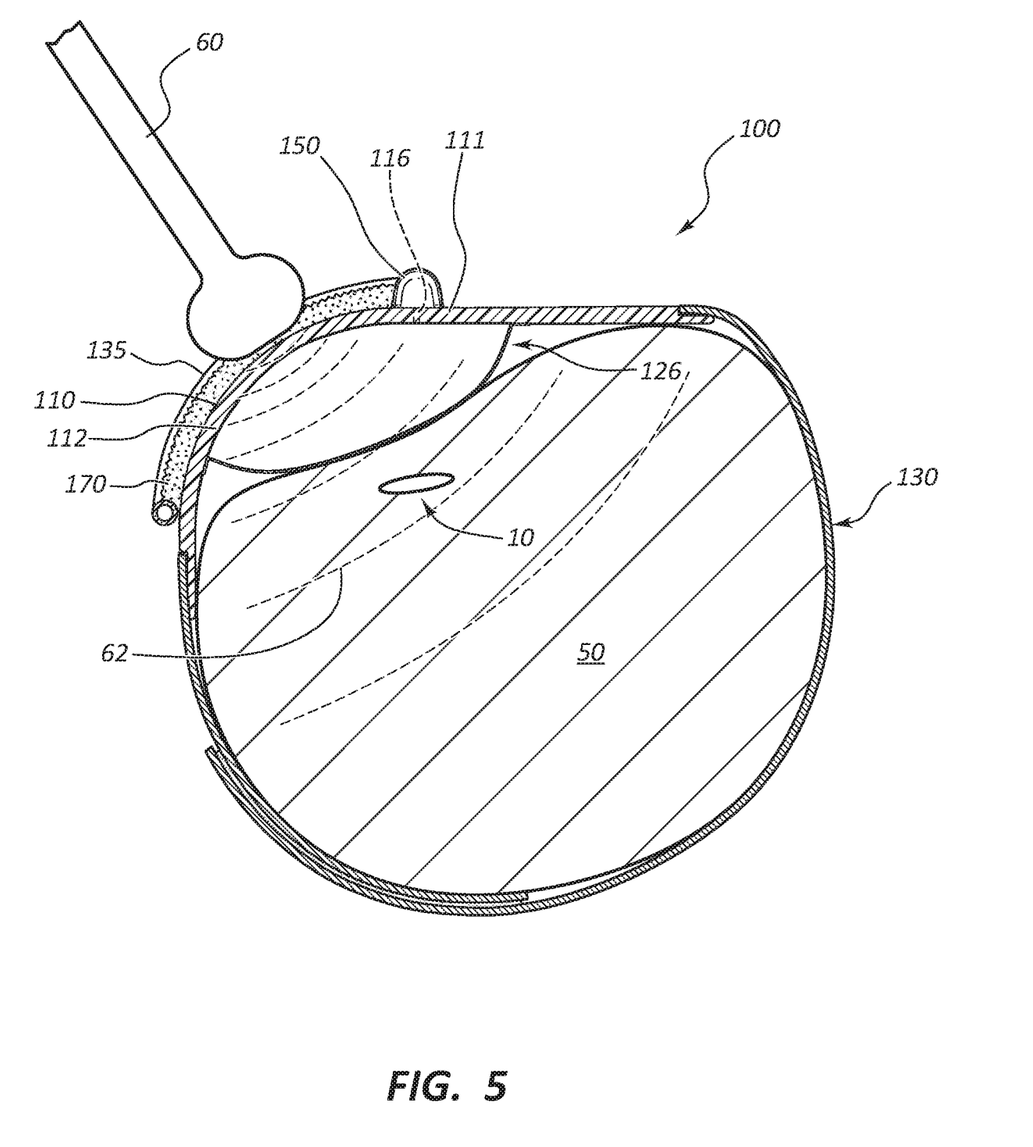
FIG. 5 is a cross-sectional side view of the vascular compression device of FIGS. 1-4 disposed around the wrist of a patient with the inflatable chamber in an inflated state.

FIGS. 1-5 provide alternative views of a vascular compression device 100. More particularly, FIG. 1 depicts a vascular compression device 100 coupled to the wrist of a patient 50. FIG. 2 provides a perspective view of an underside of the vascular compression device 100. FIG. 3 provides a side view of the vascular compression device 100. FIG. 4 provides a side view of the vascular compression device 100 with an inflatable chamber 126 in an inflated state. And FIG. 5 provides a side view of the vascular compression device 100 on a wrist of the patient 50 with the inflatable chamber 126 in an inflated state.

As shown in FIGS. 1-5, the vascular compression device 100 may include a frame 110, a flexible sheet 120, and a wristband 130.

The frame 110 may include an outer surface 111 and an inner surface 113. In some embodiments, the frame 110 may be substantially rigid. In some embodiments, the frame 110 may be fabricated from polyurethane, polyvinyl chloride, and the like. The frame 110 may be contoured to curve around a thumb-side portion of the wrist of the patient 50. For example, in some embodiments, the frame 110 includes a curved section 112 (see FIGS. 3-5). In the embodiment shown in FIGS. 1-5, the frame 110 is shaped as a curved (e.g., arched) sheet. The outer surface 111 of the frame 110 (or a portion thereof) may be convex, while the inner surface 113 of the frame 110 (or a portion thereof) may be concave. In some embodiments, the frame 110 further includes a substantially straight section 114 configured to be disposed adjacent an underside (i.e., a palmar side) of a wrist of the patient 50. In some embodiments, the frame 110 (or a portion thereof) is transparent.

In some embodiments, the curved section 112 may have a radius of curvature (r) of between 1.5 cm and 2.5 cm (see FIG. 3). Additionally or alternatively, the degree measure (θ) of an arc formed by the curved section 112 may be between 45 and 100 degrees. For example, in some embodiments, the curved section 112 is between 80 and 95 degrees (e.g., approximately 90 degrees).

The flexible sheet 120 may be coupled to the frame 110. For example, in some embodiments, the flexible sheet 120 includes a peripheral portion 122 that is attached to the frame 110 and a central portion 124 that is not attached to the frame 110. In some embodiments, the peripheral portion 122 of the flexible sheet 120 is attached to the frame 110 via welding or an adhesive. The flexible sheet 120 may be made from any suitable material, such as polyurethane or PVC. In some embodiments, the material of the flexible sheet 120 is stretchable. In the depicted embodiment, the flexible sheet 120 is substantially rectangular in shape, although other shapes are also within the scope of this disclosure. In some embodiments, the flexible sheet 120 may be pre-formed shape. In some embodiments, the flexible sheet 120 (or a portion thereof) is transparent. For example, in some embodiments, both the frame 110 (or a portion thereof) and the flexible sheet 120 (or a portion thereof) are transparent, thereby allowing a practitioner to view a vascular access site through the frame 110 and the flexible sheet 120. In some embodiments, the practitioner may need to view through only two layers (e.g., the frame 110 and the flexible sheet 120) to view the vascular access site. Viewing through only two layers may provide improved visual clarity relative to embodiments in which the vascular access site is viewed through more than two layers or parts.

The wristband 130 may be coupled to the frame 110. For example, the wristband 130 may include a first strap that is attached to one side of the frame 110 and a second strap that is attached to an opposite side of the frame 110. The wristband 130 may be configured to secure the frame 110 adjacent to the wrist of the patient 50. In some embodiments, the wristband 130 (or a portion thereof) may be opaque. In some such embodiments, the wristband 130 is colored and/or decorated. Still further, in certain embodiments, the wristband 130 may include hook and loop fasteners (e.g., Velcro). For example, in some embodiments, the wristband 130 is an integrated Velcro strap. In other embodiments, other attachment means are used to secure the vascular compression device 100 to the arm of the patient 50.

The frame 110 and the flexible sheet 120 may form the inflatable chamber 126. For example, the inner surface 113 of the frame 110 and the flexible sheet 120 may at least partially define the inflatable chamber 126. Stated differently, a wall of the inflatable chamber 126 may be defined by the frame 110. In this fashion, the inflatable chamber 126 may be defined by both a first portion (e.g., the frame 110) of the vascular compression device 100 that does not change size or shape as the inflatable chamber 126 is inflated and a second portion (e.g., the flexible sheet 120) of the vascular compression device 100 that does change in size or shape as the inflatable chamber 126 is inflated.

When the wristband 130 is coupled to the wrist of the patient 50, the inflatable chamber 126 may be positioned adjacent to a radial artery 10 of the patient 50 (see FIG. 5). (Again, as noted above, though specific examples herein refer to compression of the radial artery, devices and methods configured to compress other portions of the vasculature are within the scope of this disclosure.) In some embodiments, the vascular compression device 100 includes only a single inflatable chamber 126. The capacity of the inflatable chamber 126 may be between 3 mL and 30 mL. For example, in some embodiments, the capacity of the inflatable chamber 126 is between 3 mL and 12 mL, between 3 mL and 20 mL, between 3 mL and 25 mL, between 5 mL and 15 mL, between 10 mL and 20 mL, between 10 mL and 30 mL, or between 15 mL and 30 mL. The inflatable chamber 126 may be configured for applying varying amounts of pressure to a radial access site of the patient 50. The inflatable chamber 126 may be configured to provide pressure to the radial access site in a manner that avoids restricting the ulnar artery.

In some embodiments, the vascular compression device 100 includes tubing 135 that extends from a first aperture 116 (see FIG. 5) in the frame 110 to a valve 140. The tubing 135 and the valve 140 may be in fluid communication with the inflatable chamber 126 that is formed by the frame 110 and the flexible sheet 120. In some embodiments, the valve 140 is configured to allow fluid to flow through the valve 140 when the valve 140 is coupled to an inflation device (e.g., a syringe), but prevents fluid flow through the valve 140 when the valve 140 is not coupled (i.e., detached from) to the inflation device. In other words, the valve 140 may maintain a positive fluid pressure within the inflatable chamber 126 after the inflation device has been uncoupled from the valve 140.

In the depicted embodiment, the tubing 135 is coupled to the frame 110 via a connector 150 that protrudes from the outer surface 111 of the frame 110. In some embodiments, the tubing 135 extends from the connector 150 for a length of 5 cm to 15 cm, 6 cm to 15 cm, 8 cm to 15 cm, 10 cm to 15 cm, 12 cm to 15 cm, 6 cm to 12 cm, 6 cm to 10 cm, 6 cm to 8 cm, or 8 cm to 10 cm in length. In other words, in some embodiments, the tubing 135 is between about 5 cm to about 15 cm. In other embodiments, no tubing 135 is used. In other embodiments, the tubing 135 is of some other length.

In some embodiments, the vascular compression device 100 may further include a retainer 160 (e.g., a clip) that is configured to secure a free end of the tubing 135 to the frame 110. In some embodiments, when the vascular compression device 100 is secured to the right arm of the patient 50, the retainer 160 may be positioned (1) ulnar or radial of the connector 150 and/or (2) proximal or distal of the connector 150. For example, when the depicted embodiment is secured to the right arm of the patient 50 as shown in FIG. 1, the retainer 160 is positioned radial of and distal of the connector 150. The retainer 160 and the connector 150 may be positioned at a distance from one another such that, when a proximal end of the tubing 135 is attached to the retainer 160, only a small length of the tubing 135 protrudes from the vascular compression device 100, thereby minimizing the bulk of the vascular compression device 100.

The vascular compression device 100 may be used at or near the conclusion of a medical procedure to facilitate hemostasis of the radial artery 10. For example, in some procedures, the vascular compression device 100 may be coupled to the wrist of the patient 50, such as via the wristband 130. The practitioner may couple the vascular compression device 100 to the wrist of the patient 50 such that the inflatable chamber 126 of the vascular compression device 100 is positioned adjacent to a radial access site. For example, in some embodiments, the vascular compression device 100 is placed on the wrist around a portion of an elongate medical instrument that accesses the radial artery 10 of the patient 50 through a radial access site.

In some circumstances, the practitioner may align a first indicium 115 on the frame 110 of the vascular compression device 100 with puncture site in the skin of the patient 50. For example, the practitioner may view the radial access site through the frame 110 and the flexible sheet 120 and align the first indicium 115 on the frame 110 with the puncture site. When the first indicium 115 is aligned with the puncture site, the inflatable chamber 126 of the vascular compression device 100 may be positioned to provide compression to the arteriotomy site that is upstream of the puncture site. Stated differently, when the first indicium 115 of the vascular compression device 100 is aligned with the puncture site in the skin of the patient 50, the inflatable chamber 126 may be positioned directly over an arteriotomy site of the patient 50. In some embodiments, a second indicium (not shown) is disposed directly over the arteriotomy site when the first indicium 115 is aligned with the puncture site.

Once the vascular compression device 100 is properly placed on the arm of the patient 50, the inflatable chamber 126 may be inflated in any suitable manner. For example, in some embodiments, the practitioner may connect an inflation device (e.g., a syringe) to the valve 140. Connecting the inflation device to the valve 140 may open the valve 140, allowing the practitioner to deliver fluid into the inflatable chamber 126. For example, the practitioner may advance a plunger of a syringe that is connected to the valve 140, causing fluid to pass through the valve 140, the tubing 135, and the first aperture 116 to enter into the inflatable chamber 126. The delivery of fluid to the inflatable chamber 126 may cause the inflatable chamber 126 to expand, thereby increasing the amount of pressure that is applied to the radial access site. Stated differently, inflating the inflatable chamber 126 may increase pressure that is applied to the radial access site.

In some circumstances, the inflatable chamber 126 may first be partially inflated to provide some compression force to the radial access site. With the inflatable chamber 126 in a partially inflated state, an elongate medical device that is partially inserted into the radial artery 10 may be withdrawn from the radial artery 10 such that no medical device extends through the puncture site of the skin of the patient 50 to the arteriotomy site.

After the elongate medical device has been removed, fluid may then be delivered to the inflatable chamber 126 in an amount that is sufficient to stop bleeding at the arteriotomy site. For example, in some embodiments, sufficient fluid may be provided to fully inflate the inflatable chamber 126. Once enough fluid has been delivered to the inflatable chamber 126 to stop the bleeding, fluid within the inflatable chamber 126 may be slowly withdrawn until a flash of blood is visible at the skin puncture site through the frame 110 and the flexible sheet 120. At this stage, additional fluid (e.g., 1-2 mL) may be injected back into the inflatable chamber 126 to stop the bleeding. This process may provide adequate pressure to achieve patient hemostasis while maintaining patency of the radial artery 10. In other words, sufficient pressure is provided to prevent bleeding or a hematoma while avoiding the application of excessive force (which can unduly restrict or occlude blood flow through the radial artery 10).

Additionally, the patency of the radial artery 10 may be determined by the practitioner through the use of ultrasound. In some embodiments, such as illustrated in FIG. 5, an ultrasound probe 60 may engage with the vascular compression device 100 and ultrasound waves 62 may propagate through the vascular compression device 100 and into the biological tissues of the patient 50, in turn creating an image of the biological tissues. This imaging may then be utilized to determine the patency of the radial artery 10. The ultrasound image created from the ultrasound probe 60 may be used to visualize the patency of the radial artery 10 in real time while the inflatable chamber 126 is inflated. In some embodiments, the practitioner may inflate the inflatable chamber 126 such that the radial artery 10 is at a predetermined patency. In some embodiments, the practitioner may inflate the inflatable chamber 126 to occlude the radial artery 10 and then partially deflate the inflatable chamber 126 to allow a predetermined patency of the radial artery 10. Because the practitioner can visually determine the patency of the radial artery 10, the practitioner may leave the vascular compression device 100 in place for a prolonged period of time without concern of the radial artery 10 being occluded.

In some embodiments, the inflatable chamber 126 may be filled with a liquid configured to facilitate propagation of the ultrasound waves 62. For example, liquids such as water, saline, etc. may be used. In some embodiments, the liquid may have similar ultrasound properties as biological tissues, such as water, to help improve the resolution of the resultant ultrasound image. The inflatable chamber 126 may be filled with a volume of liquid with similar ultrasound properties as biological tissue to form an ultrasound compatible coupling between the skin of the patient and the inflatable chamber 126, thus enabling the ultrasound waves 62 to pass through the inflatable chamber 126 to the biological tissue of the patient to produce an ultrasound image. The coupling between the inflatable chamber 126 and the skin of the patient may thus eliminate the need for coupling medium (e.g., ultrasound gel) on the skin of the patient.

In some embodiments, a coupling medium or ultrasound acoustic gel 170 may be applied to the outer surface 111 of the frame 110 to improve the engagement between the ultrasound probe 60 and the frame 110. In the illustrated embodiment, ultrasound acoustic gel 170 is disposed on the surface of the frame 110. This acoustic gel 170 may reduce air pockets between the ultrasound probe 60 and the frame 110 and improve the overall ultrasound image. In some embodiments, a hydrophilic coating, including a hydrogel, may be applied to the outer surface 111 of the frame 110. In some embodiments, the hydrophilic coating may be independent of the ultrasound acoustic gel 170. In some embodiments, the hydrophilic coating may be used in addition to the ultrasound acoustic gel 170.

In some embodiments, the frame 110 may be fabricated from a low durometer rubber with similar ultrasound properties to water. The ultrasound waves 62 may travel through the low durometer rubber to help produce an ultrasound image. In some embodiments, the ultrasound acoustic gel 170 may be applied to the frame 110. In other embodiments, the material of the frame 110 may be configured to interact with the ultrasound probe 60 (for example through use of a low durometer rubber) such that ultrasound acoustic gel 170 is not necessarily applied to the frame 110. In other words, the frame 110 may be composed of a material configured to ultrasonically couple to the ultrasound probe 60 without use of an additional coupling medium. In some embodiments, a low durometer rubber may be coupled to the frame 110. The low durometer rubber may be coupled to the frame 110 via overmolding, adhesives, welding, etc.

Figure 6:
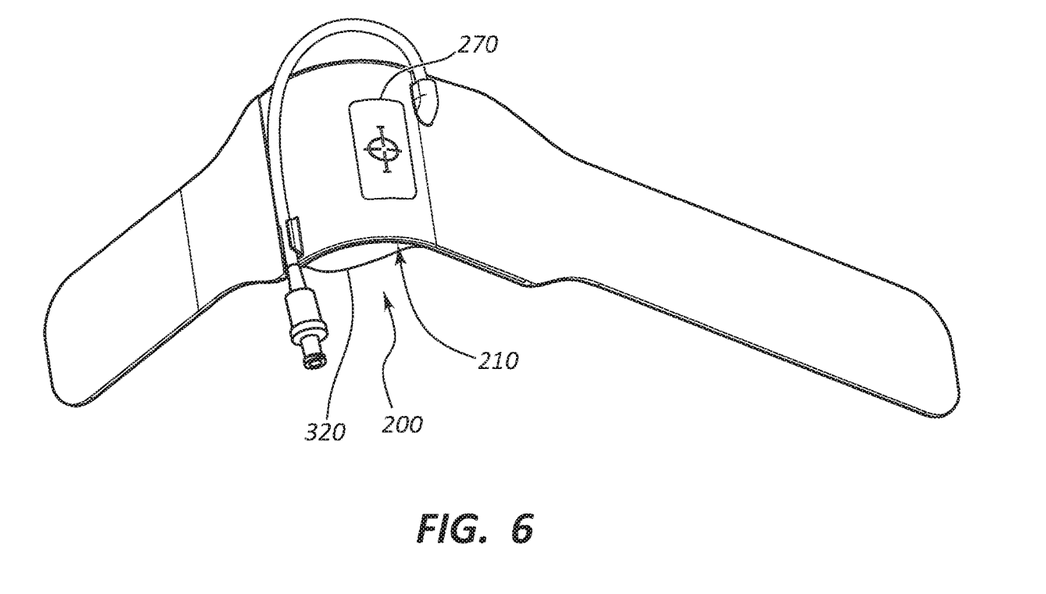
FIG. 6 is a perspective view of a vascular compression device with a window in a rigid frame of the vascular compression device.

FIG. 6 depicts an embodiment of a vascular compression device 200 that resembles the vascular compression device 100 described above in certain respects. Accordingly, like features are designated with like reference numerals, with the leading digits increment to "2." Relevant disclosure set forth above regarding similarly identified features thus may not be repeated hereafter. Moreover, specific features specific features of the vascular compression device 100 and related components shown in FIGS. 1-5 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of vascular compression device 200 and related components depicted in FIG. 6. Any suitable combination of the features, and variations of the same, described with respect to the vascular compression device 100 and related components illustrated in FIGS. 1-5 may be employed with the vascular compression device 200 and related components of FIG. 6, and vice versa. This pattern of disclosure applied equally to further embodiments depicted in subsequent figures and described hereafter, wherein the leading digits may be further incremented.

FIG. 6 illustrates another embodiment of a vascular compression device 200 that is configured to facilitate propagation of the ultrasound waves 62 through the vascular compression device 200 and to the biological tissues of the patient 50. In the embodiment of FIG. 6, a frame 210, which may be substantially rigid, includes a window 270 that is configured to enable the ultrasound probe 60 to propagate the ultrasound waves 62 through the window 270 to obtain an ultrasound image. Stated another way, the window 270 may comprise a portion of the frame 210 configured to transmit ultrasound waves while minimizing disruption. In some embodiments, the material of the window 270 may be fabricated from the same material as the frame 210, but the window 270 may be thinner than the frame 210. In such instances, because the window 270 is thinner than the frame 210, the ultrasound waves 62 from the ultrasound probe 60 may propagate better through the window 270 than through the frame 210, thus improving the quality of the ultrasound image as compared to a frame having no window. In some embodiments, the frame 210, the window 270, and a flexible sheet 220 may be fabricated from the same material.

Figure 7:
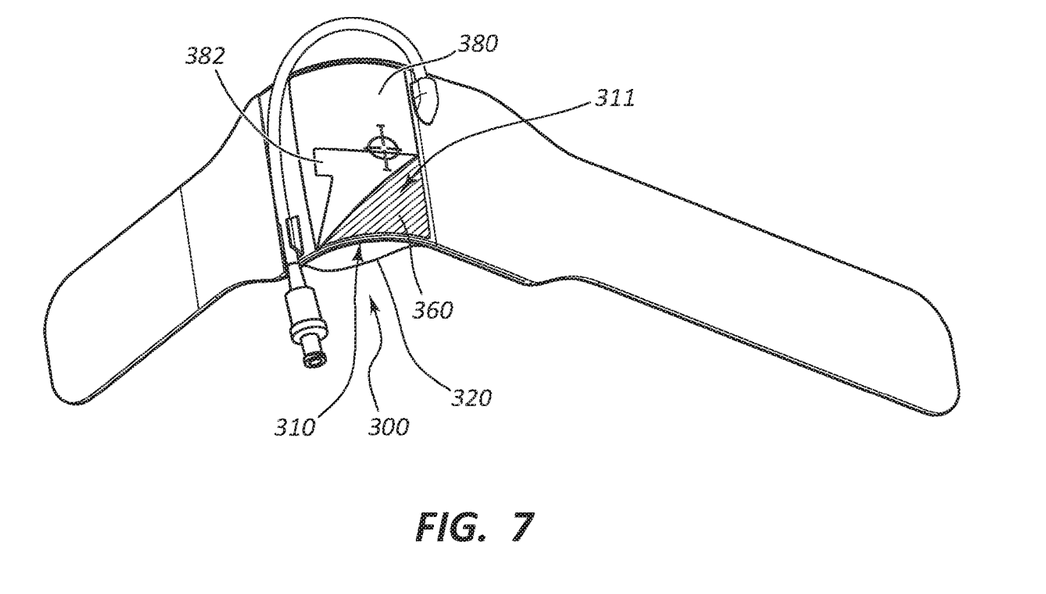
FIG. 7 is a perspective view of a vascular compression device with a peel-away layer that protects a coupling medium.

FIG. 7 illustrates another embodiment of a vascular compression device 300 that is configured to facilitate propagation of ultrasound waves 62 through the vascular compression device 300 to the biological tissues of the patient 50. A frame 310, which may be substantially rigid, may include a peel-away layer 380 that that is disposed on an outer surface 311 of the frame 310. A coupling medium or an ultrasound acoustic gel 360 may be disposed between the peel-away layer 380 and the outer surface 311 of the frame 310. The peel-away layer 380 may protect or seal the ultrasound acoustic gel 360 before the peel-away layer 380 is removed from the vascular compression device 300. The peel-away layer 380 may include a tab 382 that extends beyond an outer edge of the frame 310. In some procedures, the vascular compression device 300 is coupled to the patient 50 and positioned, and the practitioner grips the tab 382 to peel the peel-away layer 380 away from the frame 310, thus exposing the ultrasound acoustic gel 360. The exposed ultrasound acoustic gel 360 may then be used to facilitate engagement of the ultrasound probe 60 to propagate the ultrasound waves 62 through the vascular compression device 300 and the biological tissue of the patient 50.

Figure 8:
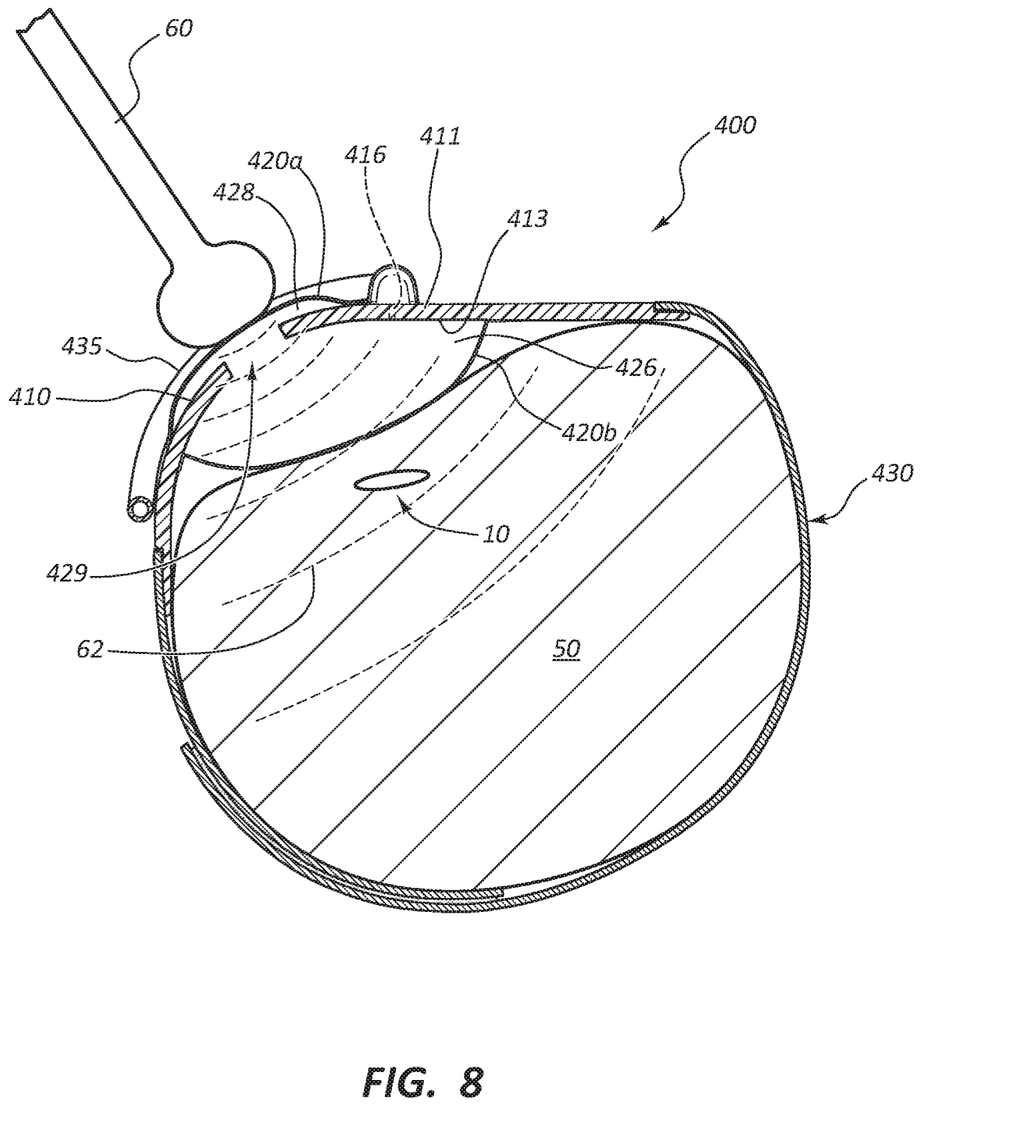
FIG. 8 is a cross-sectional side view of a vascular compression device with a flexible sheet disposed on an upper surface and a lower surface of a rigid frame around a wrist of a patient with the inflatable chamber in a fully inflated state.

FIG. 8 illustrates another embodiment of a vascular compression device 400 that is configured to facilitate propagation of ultrasound waves 62 through the vascular compression device 400 and the biological tissues of the patient 50. In some instances, ultrasound waves 62 may become distorted when traveling through multiple layers of materials. Thus, in some embodiments, a vascular compression device, such as vascular compression device 400, may be configured to minimize the layers through which ultrasound waves pass during use of the compression device. The vascular compression device 400 of FIG. 8 includes a frame 410, which may be substantially rigid, an outer flexible sheet 420a, and inner flexible sheet 420b, and a wristband 430. The outer flexible sheet 420a may be disposed on an outer surface 411 of the frame 410 and the inner flexible sheet 420b an inner surface 413 of the frame 410, thus creating two inflatable chambers, an inner inflatable chamber 426 and an outer inflatable chamber 428. An aperture 429 may be disposed in the frame 410 that connects the inner inflatable chamber 426 and the outer inflatable chamber 428.

In some embodiments, the aperture is disposed in the frame 410 at a location that achieves a line of sight to the radial artery 10. Accordingly, along portion of the vascular compression device 400 where the aperture 429 is disposed, the ultrasound wave 62 only passes through the inflatable chambers 426 and 428 before reaching the biological tissues, thus minimizing the layers the ultrasound wave 62 pass through. In other words, the aperture 429 may be positioned such that it creates an ultrasound transmission window through the frame 410. In some embodiments, the portion of the frame 410 disposed along the inflatable chambers 426 and 428 may be thinner than the portion of the frame 410 that couples the flexible sheets 420a and 420b to the frame 410. The thinner portion of the frame 410 facilitate engagement of the ultrasound probe 60 as the thinner portion may be more flexible and/or less disruptive to transmission of ultrasound waves.

Once the vascular compression device 400 is disposed on the arm of the patient 50, the inner inflatable chamber 426 may be inflated in any suitable manner. For example, in some embodiments, the practitioner may connect an inflation device (e.g., a syringe) to the valve (not shown). Connecting the inflation device to the valve may open the valve, allowing the practitioner to deliver fluid into the inner inflatable chamber 426. For example, a practitioner may advance a plunger of a syringe that is connected to the valve, causing fluid to pass through the valve, a tubing 435, and a first aperture 416 to enter into the inner inflatable chamber 426 and the outer inflatable chamber 428 through the aperture 429. The delivery of fluid to the inner and outer inflatable chambers 426 and 428 may cause the inner and outer inflatable chambers 426 and 428 to expand, thereby increasing the amount of pressure that is applied to the radial access site. The fluid may be a fluid with ultrasound properties similar to biological tissue, such as water.

The embodiment of FIG. 8 may thus be configured to provide a surface for engaging an ultrasound probe 60 as well as reducing the layers of material through which an ultrasound wave passes between the ultrasound probe 60 and the artery to be imaged. Regarding the first point, the outer inflatable chamber 428 may be configured to provide a compliant surface for engaging the ultrasound probe 60. In some embodiments, an ultrasound probe 60 may be placed in contact with the outer flexible sheet 420a without the use of coupling gels or other intermediate agents. Furthermore, and to the second point, the ultrasound probe 60, when in direct contact with the outer inflatable chamber 428 may be positioned to minimize the layers and material of the compression device 400 disposed between the ultrasound probe 60 and the anatomy to be imaged. In the illustrated embodiment, the ultrasound probe 60 contacts the outer flexible sheet 420a and an ultrasound wave need only pass through the outer flexible sheet 420a, the liquid disposed within the inflatable chambers 428 and 426 (which create an uninterrupted volume of fluid along the path of the ultrasound wave due to the aperture 429 as discussed below), and the inner flexible sheet 420b.

The aperture 429 in the frame 410 may thus reduce the numbers of layers for the ultrasound waves 62 to pass through at certain locations, thus potentially improving ultrasound image produced. In some embodiments, there may be a plurality of the apertures 429 disposed in the frame 410. In some embodiments, there is no aperture 429 between the inner inflatable chamber 426 and the outer inflatable chamber 428, and the outer inflatable chamber 428 may be pre-inflated, or inflated with fluid separately from the inner inflatable chamber 426. In some embodiments, the ultrasound wave 62 passes through material two layers of the vascular compression device 400, such as through the outer flexible sheet 420a and the inner flexible sheet 420b. As discussed herein the volume of fluid within the inflatable chambers 428 and 426 acts as a coupling medium between the outer flexible sheet 420a and the inner flexible sheet 420b, but does not constitute a material layer of the vascular compression device 400

While the compression devices described above are described as radial artery compression devices, some compression devices may, additionally or alternatively, be suitable for compression of an ulnar artery. For example, a compression device may be placed on the patient such that the frame curves around the ulnar side of the wrist. When placed on the patient in this manner, the inflatable chamber may be positioned adjacent to the ulnar artery such that inflation of the inflatable chamber applies pressure directly to, adjacent to, or slightly upstream of an access site in the ulnar artery. Thus, some compression devices described herein may be used to promote healing at access sites in an ulnar artery.

Figure 9:
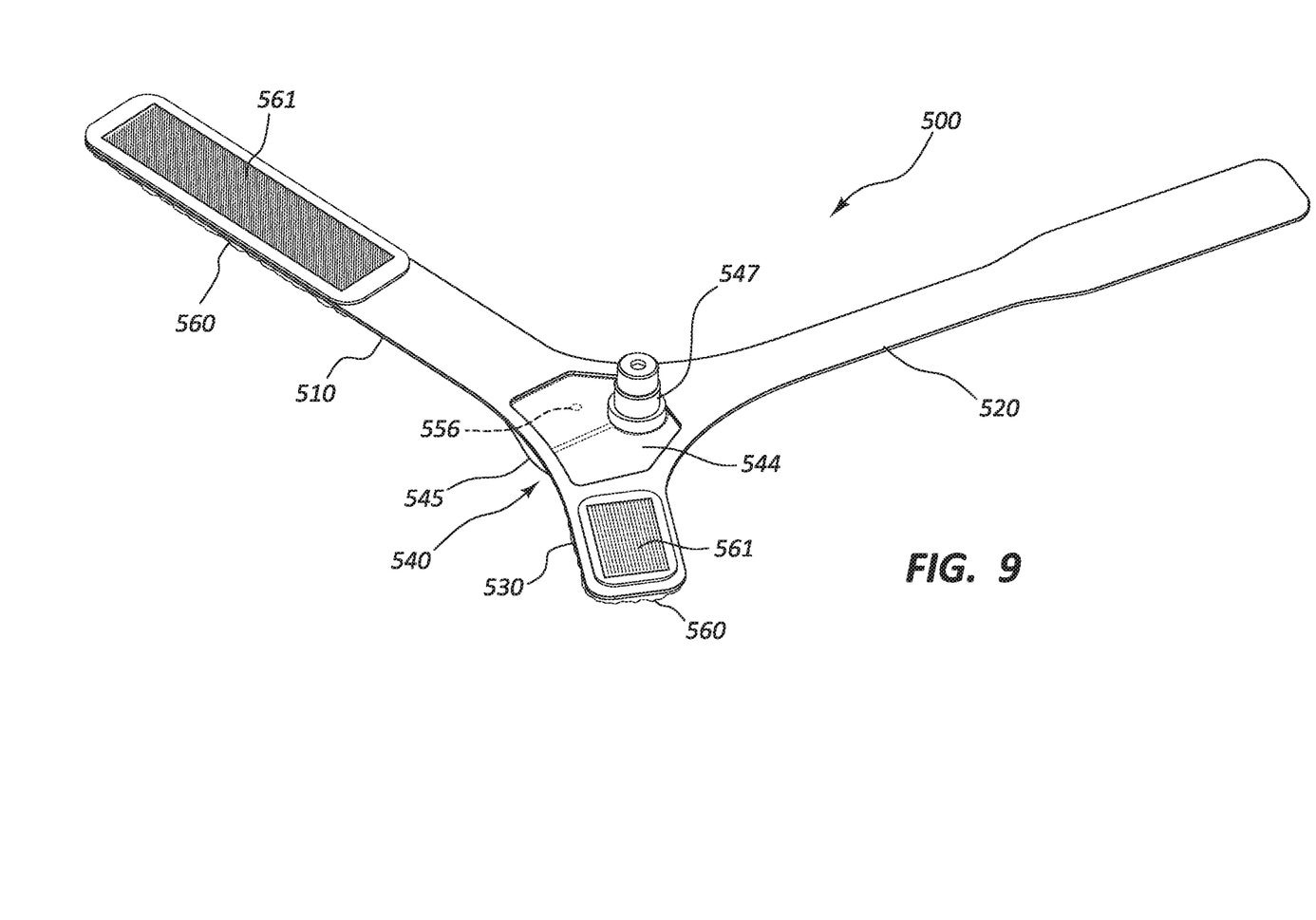
FIG. 9 is a perspective view of another exemplary vascular compression device.

FIG. 9 provides a view of a vascular compression device 500. The vascular compression device 500 may comprise a hand band or strap 510, a thumb band or strap 520, a securement band or strap 530, and a compression member 540. The vascular compression device 500 may be configured to fit around a proximal portion of a hand and around a thumb to provide compression to a vascular access puncture site of a distal portion of a radial artery in the anatomical snuffbox area of a patient's hand. The vascular compression device 500 may be configured to be a left hand device or a right hand device such that the vascular compression device 500 may provide hemostasis at a distal radial artery puncture site in the left or right hand. FIG. 9 illustrates a hemostasis device configured for use on the right hand of the patient. In some embodiments, the vascular compression device 500 may comprise additional bands to facilitate coupling of the vascular compression device 500 to the hand.

The hand band 510 may be formed from a flexible material, such as a plastic film, cloth, etc. The hand band 510 may comprise a releasable securement mechanism, such as a hook-and-loop material comprised of a loop material 560 configured to attach to a hook material 561. In some embodiments, the loop material 560 and/or the hook material 561 may be integral to the material of the hand band 510. In other embodiments, the loop material 560 and/or the hook material 561 may be coupled to a top surface and/or bottom surface of the hand band 510 using any suitable technique, such as sonic welding, heat welding, adhesives, etc. The loop material 560 and/or the hook material 561 may cover the top or bottom surfaces of the hand band 510 from a first end to a second end. In other embodiments, the loop material 560 and/or the hook material 561 may cover a portion of the hand band 510.

The compression member 540 may comprise a top plate 544, an inflatable bladder 545, and an inflation port 547. The inflatable bladder 545 may be coupled to a bottom portion of the top plate 544 such that edges of the inflatable bladder 545 form a fluid-tight seal. The inflatable bladder 545 may comprises a flexible wall configured to extend downward from the top plate 544 to form an inflatable chamber when the inflatable bladder 545 is filled with air or fluid such that a compressive force may be applied to the vascular access puncture site. The inflatable bladder 545 may be transparent or translucent such that the puncture site can be seen through the top plate 544 and the inflatable bladder 545 to determine proper placement of the inflatable bladder 545 over the puncture site and hemostasis status during treatment. The inflatable bladder 545 may comprise a target 556 printed on or adhered to a surface of the inflatable bladder 545, including a bottom surface of the inflatable bladder 545. The target 556 may be configured to facilitate placement of the inflatable bladder 545 over the puncture site. The inflatable bladder 545 may be formed from a flexible, translucent or transparent material such as polyethylene, polypropylene, polyvinyl chloride, etc.

The vascular compression device 500 described in FIG. 9 may be modified or utilized in any of the ways previously described in regard to the embodiments of FIGS. 5-8 to facilitate obtaining an ultrasound image. For example, an ultrasound acoustic gel may be applied to the top plate 544 of the vascular compression device 500 to enable an ultrasound probe to propagate ultrasound waves through the vascular compression device 500 and the biological tissue of a patient. In another embodiment, the top plate 544 may include a window that is thinner than other portions of the top plate 544. Further, the top plate 544 may have a peel-away layer that may be removed from the top plate 544 to expose an ultrasound acoustic gel, thus enabling an ultrasound probe to engage with the gel. The peel-away layer may be removed by the practitioner after the vascular compression device 500 is coupled to the patient and positioned. In another embodiment, the vascular compression device 500 may include an inner inflation chamber and an outer inflation chamber with apertures in the top plate 544 to minimize the number of layers the ultrasound waves pass through and to create an engaging surface for an ultrasound probe.

Additionally, it is within the scope of this disclosure to utilize the components, methods, and concepts herein with a wide variety of compression device designs and applications, including devices with various structures and devices configured for various uses.

Additional structure features of various embodiments of vascular compression devices may be found in U.S. patent application Ser. No. 15/648,110, filed Jul. 12, 2017, titled "Inflatable Radial Artery Compression Device," U.S. patent application Ser. No. 15/705,759, titled "Method of Manufacturing an Inflatable Compression Device," and U.S. Provisional Patent Application No. 62/625,626, titled "Hemostasis Devices and Methods of Use," all of which are incorporated by reference in their entirety.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A vascular compression device, the vascular compression device comprising:
    a substantially rigid frame, the frame comprising an outer surface and an inner surface;
    a flexible sheet coupled to the frame;
    a chamber at least partially defined by the inner surface of the frame and the flexible sheet;
    a coupling medium disposed on the outer surface of the frame;
    a second flexible sheet coupled to the outer surface of the frame; and
    a second chamber at least partially defined by the outer surface of the frame and the second flexible sheet,
    wherein the second chamber is disposed outside the frame, and
    wherein the second chamber is configured to be inflated with a liquid.

2. The vascular compression device of claim 1, wherein the chamber is configured to be inflated with a liquid.

3. The vascular compression device of claim 1, wherein an ultrasound wave passes through two layers or less of the vascular compression device including at least the chamber.

4. The vascular compression device of claim 1, wherein along a portion of the vascular compression device, an ultrasound probe is engagable with an upper surface of the second chamber and some of the ultrasound waves from the ultrasound probe only pass through the chamber, the second chamber, and the coupling medium.

5. The vascular compression device of claim 1, wherein the frame further comprises a window, wherein the window is thinner than the frame.

6. The vascular compression device of claim 1, wherein the coupling medium is an acoustic ultrasound gel.

7. The vascular compression device of claim 1, wherein the coupling medium is a hydrophilic coating.

8. The vascular compression device of claim 1, wherein the frame further comprises a peel-away layer on the outer surface of the frame, and
    wherein the coupling medium is disposed between the outer surface of the frame and the peel-away layer.

9. The vascular compression device of claim 1, wherein the frame further comprises an aperture that enables communication between the chamber and the second chamber.

10. The vascular compression device of claim 1, further comprising indicia on the frame, wherein the indicia are designed to facilitate identification of an arteriotomy site relative to a puncture site in a patient's skin.

11. A vascular compression device, the vascular compression device comprising:
    a substantially rigid frame, the frame comprising an outer surface and an inner surface;
    a flexible sheet that is coupled to the frame; and
    an inflatable chamber that is at least partially defined by the inner surface of the frame and the flexible sheet,
    wherein the inflatable chamber is configured to be inflated with water, and
    wherein along a portion of the vascular compression device, the inflatable chamber has an upper surface and a lower surface and an ultrasound probe is engagable with the upper surface of the inflatable chamber and some of the ultrasound waves from the ultrasound probe only pass through the inflatable chamber.

12. The vascular compression device of claim 11, wherein an ultrasound wave passes through two layers or less of the vascular compression device including at least the inflatable chamber.

13. The vascular compression device of claim 11, wherein the frame further comprises a window, wherein the window is thinner than the frame.

14. The vascular compression device of claim 11, further comprising:
    a second flexible sheet coupled to the outer surface of the frame;
    a second inflatable chamber that is at least partially defined by the outer surface of the frame and the second flexible sheet; and
    an aperture disposed in the frame that enables communication between the inflatable chamber and the second inflatable chamber.

* * * * *